US012285515B2

(12) United States Patent
Fidge et al.

(10) Patent No.: US 12,285,515 B2
(45) Date of Patent: *Apr. 29, 2025

(54) MICROCAPSULE AND HAIR CARE COMPOSITION

(71) Applicant: Conopco, Inc., Englewood Cliffs, NJ (US)

(72) Inventors: Christopher Fidge, Wirral (GB); Stephen Golding, Northwich (GB); Stefan Antonius Franciscus Bon, Coventry (GB); Samuel Richard Wilson-Whitford, Bethlehem, PA (US); James Merrington, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/639,385

(22) PCT Filed: Aug. 25, 2020

(86) PCT No.: PCT/EP2020/073707
§ 371 (c)(1),
(2) Date: Mar. 1, 2022

(87) PCT Pub. No.: WO2021/043627
PCT Pub. Date: Mar. 11, 2021

(65) Prior Publication Data
US 2022/0331227 A1 Oct. 20, 2022

(30) Foreign Application Priority Data
Sep. 6, 2019 (EP) .................................... 19196053

(51) Int. Cl.
A61K 8/84 (2006.01)
A61K 8/11 (2006.01)
A61K 8/49 (2006.01)
A61Q 5/00 (2006.01)
A61Q 5/02 (2006.01)

(52) U.S. Cl.
CPC ................ A61K 8/84 (2013.01); A61K 8/11 (2013.01); A61K 8/4926 (2013.01); A61Q 5/006 (2013.01); A61Q 5/02 (2013.01); A61K 2800/412 (2013.01); A61K 2800/56 (2013.01)

(58) Field of Classification Search
CPC .......... A61K 8/84; A61K 8/11; A61K 8/4926; A61K 2800/412; A61K 2800/56; A61Q 5/006; A61Q 5/02
See application file for complete search history.

(56) References Cited

U.S. PATENT DOCUMENTS

| 3,958,581 A | 5/1976 | Abegg et al. |
| 3,962,418 A | 6/1976 | Birkofer |
| 4,009,256 A | 2/1977 | Nowak, Jr. et al. |
| 5,194,639 A | 3/1993 | Connor et al. |
| 2002/0172648 A1 | 11/2002 | Hehner et al. |
| 2013/0017239 A1 | 1/2013 | Viladot Petit et al. |
| 2013/0330292 A1 | 12/2013 | Lei et al. |
| 2016/0060427 A1 | 3/2016 | Steinbrecher et al. |
| 2016/0075912 A1* | 3/2016 | Steinbrecher ...... C08G 18/0819 524/839 |
| 2016/0310393 A1* | 10/2016 | Chang ..................... A61K 8/442 |
| 2017/0027823 A1 | 2/2017 | Weissbrodt et al. |
| 2018/0272308 A1 | 9/2018 | Sasaki et al. |
| 2019/0008734 A1* | 1/2019 | Dubovoy ................. A61K 8/34 |
| 2019/0054440 A1* | 2/2019 | Mistry .................... C08F 20/20 |
| 2022/0323922 A1 | 10/2022 | Fidge et al. |

FOREIGN PATENT DOCUMENTS

| CN | 108350181 | 7/2018 |
| EA | 028996 | 1/2018 |
| EP | 1702674 | 9/2006 |
| JP | 2016518497 | 6/2016 |
| JP | 2019529646 | 10/2019 |
| JP | 2022547054 | 11/2022 |
| WO | WO9206154 | 4/1992 |
| WO | WO9522311 | 8/1995 |
| WO | WO2008145547 | 12/2008 |
| WO | WO2013026656 | 2/2013 |
| WO | WO2013026657 | 2/2013 |
| WO | WO2014064121 | 5/2014 |
| WO | WO2015078943 | 6/2015 |
| WO | WO2016058837 | 4/2016 |
| WO | WO2017058875 | 4/2017 |
| WO | WO2017084826 | 5/2017 |
| WO | WO-2017085033 A1 * | 5/2017 |
| WO | WO2017123965 | 7/2017 |

(Continued)

OTHER PUBLICATIONS

National Center for Biotechnology Information (2024). PubChem Compound Summary for CID 3893, Lauric Acid. Retrieved Apr. 3, 2024 from https://pubchem.ncbi.nlm.nih.gov/compound/Lauric-Acid. (Year: 2024).*
National Center for Biotechnology Information (2024). PubChem Compound Summary for CID 5281, Stearic Acid. Retrieved Apr. 3, 2024 from https://pubchem.ncbi.nlm.nih.gov/compound/Stearic-Acid. (Year: 2024).*
Search Report and Written Opinion in EP19196053; Feb. 7, 2020.
Search Report and Written Opinion in EP19196043.4; Feb. 7, 2020.
Search Report and Written Opinion in PCTEP2020073707; Oct. 26, 2020.
Search Report and Written Opinion in PCTEP2020073708; Oct. 26, 2020.

Primary Examiner — Doan T Phan
(74) Attorney, Agent, or Firm — Byrne Poh LLP; Nina R. Horan

(57) ABSTRACT

A core shell microcapsule having a liquid core and an outer shell, in which the liquid core comprises solvent and a piroctone compound and the shell comprises polyurea comprising amino sulphonic acid.

16 Claims, No Drawings

(56) References Cited

FOREIGN PATENT DOCUMENTS

| WO | WO2018050914 | 3/2018 |
| WO | WO2019063515 | 4/2019 |
| WO | WO2019096601 | 5/2019 |

* cited by examiner

MICROCAPSULE AND HAIR CARE COMPOSITION

CROSS-REFERENCE TO RELATED APPLICATIONS

This application is a U.S. National Phase Application under 35 U.S.C. § 371 of International Application No. PCT/EP2020/073707, filed on Aug. 25, 2020, which claims priority to European Patent Application No. EP19196053.3 filed Sep. 6, 2019, the entire disclosures of which are incorporated herein by reference in their entireties, for any and all purposes.

TECHNICAL FIELD

This invention relates to a microcapsule comprising a piroctone compound, to a process to make the microcapsule comprising piroctone compound and to anti-dandruff hair care compositions. In particular compositions comprising surfactant and piroctone compound as anti-dandruff active.

BACKGROUND

Dandruff is a problem affecting many globally. The condition is manifested by the shedding of clumps of dead skin cells from the scalp. These are white in colour and provide an aesthetically displeasing appearance. A factor that contributes to dandruff are certain members of the *Malassezia* yeasts. To combat these, hair treatment compositions are developed including various actives for their antidandruff effectiveness. Piroctone compound such as piroctone olamine is one such active.

To aid deposition and to increase the effectiveness of an antidandruff active, it some instances the antidandruff agent may be encapsulated.

Encapsulation of antidandruff agents is disclosed in EP 1 702 674 (Cognis).

WO2017/084826 (Unilever) discloses a core shell microcapsule wherein the liquid core of the microcapsule comprises solvent and the antidandruff agent climbazole dissolved in the solvent.

However, there remains the need for a stable system to encapsulate piroctone compounds and which releases piroctone slowly on drying. It is believed slow-release of active on drying will give a longer-lasting antidandruff benefit.

DESCRIPTION OF THE INVENTION

According to the present invention there is provided a core shell microcapsule having a liquid core and an outer shell, in which the liquid core comprises solvent and a piroctone compound and the shell comprises polyurea comprising amino sulphonic acid.

Without being bound by theory it is thought that the addition of the amino-sulphonic acid into the shell polymer has the effect of reducing the degree to which the microcapsule collapses on drying on the scalp, and hence increases the longevity of the effect of sebum-soluble antidandruff actives.

The invention also relates to a hair care composition comprising surfactant and at least 0.05 wt % of the total composition of a core shell microcapsule described above.

DETAILED DESCRIPTION OF THE INVENTION

The composition of the present invention comprises a core shell microparticle in which the polyurea of the shell is formed from amino sulphonic acid.

Preferably the polyurea shell comprises monomeric units of isocyanates and amines in addition to the amino sulphonic acid. It is preferred if the isocyanate is aliphatic, more preferably it is aliphatic and cyclic or branched.

The amine unit used to form the polyurea may be monomeric in nature or a polymeric amine.

Preferably the aliphatic isocyanate monomer used to prepare the polyurea comprises isopherone diisocyanate and/or hexamethylene diisocyanate.

The polyurea shell comprises an amino sulphonic acid, preferably the amino sulphonic acid is taurine.

Preferably the amino sulphonic acid is added during preparation of the polyurea shell at a level at least at 0.1 wt % relative to isocyanate, more preferably at least 1 wt % relative to isocyanate and most preferably at 5 wt % relative to isocyanate.

Preferably the amine used to prepare the polyurea further comprises diethylene triamine, tris(2-aminoethyl)amine, bis (hexamethylene) triamine and/or polyethylene imine.

The polymerisation process may use a Pickering emulsion type process. Such a process is taught in WO 2008/145547. Shell chemistries known to the skilled person that are based on Pickering emulsion processes are melamine formaldehyde, urea formaldehyde and melamine glyoxal. Alternatively, the polymerisation process may be done by interfacial polymerisation. A suitable process for making polyurea microcapsules is taught in US2013/330292. Shell chemistries to form the polyurea of the present invention are known to the skilled person that are based on interfacial polymerisation are polyurea formed by reaction of polyisocyanates and polyamines.

The diameter of the core shell microcapsules is preferably at least 5 microns. The diameter should be less than 50 microns as if it is larger than that the particles become visible to the naked eye. Preferably, microcapsule diameters lie in the range, 5 to 20 micron, more preferably from 10 to 15 micron.

A deposition aid with affinity for hair root or scalp may be grafted on to the outside of the microcapsule shell. Preferred deposition aids and grafting methods for the preferred shell materials are taught elsewhere and are known to the skilled worker. Most preferred are: grafted dextran; HPC (and the other hydrophobically modified polysaccharides); more preferred are chitosan salts. WO 14/064121 discloses use of a chitosan salt as a deposition aid for increasing deposition of microcapsules onto hair, WO 13/026656 discloses use of dextran as a deposition aid for use to deposit microcapsules from a hair shampoo and WO 13/026657 discloses use of HPMC and HEMC as deposition aids to assist deposition of microcapsules from a hair shampoo.

Advantageously a deposition aid is added either before or during step (d) to covalently bond to the surface of the microcapsules. Alternatively, a spacer may be bonded to the surface of the microcapsules and a deposition aid then reacted onto the spacer. Polyethylene glycol is a suitable spacer. Preferred deposition aids are selected from the group consisting of: grafted dextran, HPC (and the other hydrophobically modified polysaccharides) and peptides. Cationic polymers are preferred in particular chitosan.

Also according to the present invention there is provided a hair shampoo comprising surfactant and at least 0.05 wt % of the total composition a core shell microcapsule, preferably from 0.1 to 1.0 wt.

The ratio of solvent to piroctone compound within the shell microcapsule comprising is at least 15:1, preferably at least 11:1.

The piroctone compound for use in the present invention include piroctone acid, primary, secondary and tertiary olamine salts of piroctone acid (such as the diethanolamine and triethanolamine salts), and mixtures thereof, preferably piroctone acid, primary olamine salt of piroctone acid (i.e. piroctone olamine, also known as Octopirox®) and mixtures thereof, more preferably piroctone acid.

The Solvent

It is essential that the solvent within the core shell microparticle can dissolve piroctone compound efficiently or the number of microcapsules needed in a hair care composition will become intolerably high. Preferred solvents ae aromatic. The preferred minimum dissolving power for the present invention is such that at most 8 times, preferably at most 5 times as much solvent is used as piroctone compound is dissolved. Once dissolved it is important that the piroctone compound stays in solution as this aids transport of the piroctone compound once the microcapsule fractures and delivers its liquid core payload. Preferred solvents comprise perfume components and in that case they will comprise at least 50 wt % mid notes and low notes to give low volatility so that the dissolved piroctone compound remains in solution after rupture of the microcapsule. Thus, the solvent system should avoid volatile solvents whose use causes the piroctone compound to crystallise out of an open test solution in less than 1 hour at 25° C. The c Log P of the solvent should preferably be greater than 1.8, more preferably greater than 2, and most preferably greater than 3. A suitable solvent that can be used in admixture or alone is heptanone.

Piroctone Compound Level

The level of piroctone compound in the microcapsule should be as high as possible without it coming out of solution. For the preferred solvent systems the level per particle will typically be at least twice that of the latex particles of the prior art. This means that the amount of delivery system is reduced compared with that prior art.

Preferably, the piroctone compound is present at from 0.01 to 1 wt % of the composition, more preferably from 0.05 to 0.6 wt % and most preferably from 0.01 to 0.5 wt % of the composition.

The Surfactant System

The composition may be in any common product form used as a hair care product to treat hair. Preferably, it is a rinse off composition and most preferably, it is an anti-dandruff shampoo composition.

The composition may comprise any of the ingredients commonly found in hair care products depending on the product form.

For example, when the composition is a shampoo it will comprise a surfactant system including at least one cleansing surfactant suitable for use in shampoos. When it is a composition which aims to provide conditioning benefit, it will comprise a conditioning active. Suitable conditioning actives include fatty alcohols, silicones and cationic surfactants.

Examples of suitable anionic cleansing surfactants are the alkyl sulphates, alkyl ether sulfates, alkaryl sulfonates, alkanoyl isethionates, alkyl succinates, alkyl sulfosuccinates, alkyl ether sulfosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulfates, alkyl ether sulfosuccinates, alkyl ether phosphates and alkyl ether carboxylic acids and salts thereof may contain from 1 to 20 ethylene oxide or propylene oxide units per molecule.

Typical anionic cleansing surfactants for use in compositions of the invention include sodium oleyl succinate, ammonium lauryl sulfosuccinate, sodium lauryl sulfate, sodium lauryl ether sulphate, sodium lauryl ether sulphosuccinate, ammonium lauryl sulfate, ammonium lauryl ether sulfate, sodium dodecylbenzene sulfonate, triethanolamine dodecylbenzene sulfonate, sodium cocoyl isethionate, sodium lauryl isethionate, lauryl ether carboxylic acid and sodium N-lauryl sarcosinate.

Preferred anionic surfactants are the alkyl sulfates and alkyl ether sulfates. These materials have the respective formulae $ROSO_3M$ and $R-O(C_2H_4O)_xSO_3M$, wherein R is alkyl or alkenyl of from 8 to 18 carbon atoms, x is an integer having a value of from about 1 to about 10, and M is a cation such as ammonium, alkanolamines, such as triethanolamine, monovalent metals, such as sodium and potassium, and polyvalent metal cations, such as magnesium, and calcium. Most preferably, R has 12 to 14 carbon atoms, in a linear rather than branched chain.

Preferred anionic cleansing surfactants are selected from sodium lauryl sulfate and sodium lauryl ether sulfate(n)EO, (where n is from 1 to 3); more preferably sodium lauryl ether sulfate(n)EO, (where n is from 1 to 3); most preferably sodium lauryl ether sulfate1EO.

Preferably the level of alkyl ether sulfate is from 0.5 wt % to 25 wt % of the total composition, more preferably from 3 wt % to 18 wt %, most preferably from 6 wt % to 15 wt % of the total composition.

The total amount of anionic cleansing surfactant in compositions of the invention generally ranges from 0.5 wt % to 45 wt %, more preferably from 1.5 wt % to 20 wt %.

Compositions of the invention may contain non-ionic surfactant. Most preferably, non-ionic surfactants are present in the range 0 to 5 wt %.

Non-ionic surfactants that can be included in compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups. Alkyl ethoxylates are particularly preferred. Most preferred are alkyl ethoxylates having the formula $R-(OCH_2CH_2)_nOH$, where R is a $C_{12-15}$ alkyl chain and n is 5 to 9.

Other suitable non-ionic surfactants include mono- or di-alkyl alkanolamides. Examples include coco mono- or di-ethanolamide and coco mono-isopropanolamide.

Further non-ionic surfactants which can be included in shampoo compositions of the invention are the alkyl polyglycosides (APGs). Typically, APG is one which comprises an alkyl group connected (optionally via a bridging group) to a block of one or more glycosyl groups. Preferred APGs are defined by the following formula:

$RO-(G)_n$ wherein R is a branched or straight chain alkyl group which may be saturated or unsaturated and G is a saccharide group. R may represent an alkyl chain with a mean length of from about $C_5$ to about $C_{20}$. Most preferably R represents an alkyl chain with a mean length of from about $C_{9.5}$ to about $C_{10.5}$. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex BASF (DeWolf).

Other sugar-derived non-ionic surfactants which can be included in compositions of the invention include the $C_{10}$-$C_{18}$N-alkyl ($C_1$-$C_6$) polyhydroxy fatty acid amides, such as the $C_{12}$-$C_{18}$N-methyl glucamides, as described for example in WO 92 06154 and U.S. Pat. No. 5,194,639, and the N-alkoxy polyhydroxy fatty acid amides, such as C10-C18N-(3-methoxypropyl) glucamide.

Amphoteric or zwitterionic surfactant can be included in an amount ranging from 0.5 wt % to about 8 wt %, preferably from 1 wt % to 4 wt % of the total shampoo composition.

Examples of amphoteric or zwitterionic surfactants include alkyl amine oxides, alkyl betaines, alkyl amidopropyl betaines, alkyl sulfobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulfopropyl betaine, lauryl betaine, cocamidopropyl betaine and sodium cocoamphoacetate.

A particularly preferred amphoteric or zwitterionic surfactant is cocamidopropyl betaine. Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

Particularly preferred compositions comprise a surfactant system comprising: 10 to 20 wt % of the composition sodium lauryl sulphate or sodium lauryl ether sulphate (n) EO, (where n ranges from 1 to 3); 0.5 to 5 wt % of the composition cocamidopropylbetaine; and 0.5 to 5 wt % of the composition sodium cocoamphoacetate or sodium lauryl cocoamphoacetate.

Other Ingredients

The compositions may also include one or more of the following non-essential ingredients:

PH Adjusters

The pH of the compositions is preferably in the range of from 5 to 8, more preferably in the range of from 6 to 7 e.g., 6.5. The pH of the compositions can be adjusted using alkaline agents (such as sodium hydroxide, for example) or acidic agents (such as citric acid) as is well-known in the art.

Cationic Polymer

A cationic polymer is a preferred ingredient in the hair care compositions according to the invention, for enhancing conditioning performance of the compositions.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus, when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

a) copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, NJ, USA) under the LUVIQUAT tradename (e.g. LUVIQUAT FC 370);

b) copolymers of 1-vinyl-2-pyrrolidine and dimethylaminoethyl methacrylate, referred to in the industry (CTFA) as Polyquaternium-11. This material is available commercially from Gaf Corporation (Wayne, NJ, USA) under the GAFQUAT tradename (e.g., GAFQUAT 755N);

c) cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

d) mineral acid salts of amino-alkyl esters of homo- and co-polymers of unsaturated carboxylic acids having from 3 to 5 carbon atoms, (as described in U.S. Pat. No. 4,009,256);

e) cationic polyacrylamides (as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

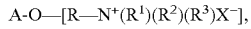

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, NJ, USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, NJ, USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR C15, JAGUAR C17 and JAGUAR C16 and JAGUAR C162. The presence of a cationic polymer is believed to enhance deposition of encapsulates comprising grafted HPC deposition aid.

The cationic conditioning polymer will generally be present in compositions of the invention at levels of from 0.01 to 5, preferably from 0.05 to 1, more preferably from 0.08 to 0.5 wt % of the composition.

When cationic conditioning polymer is present in a hair care composition according to the invention, it is preferred if the copolymer is present as emulsion particles with a mean diameter ($D_{3,2}$ as measured by light scattering using a Malvern particle sizer) of 2 micrometres or less.

Hair care compositions of the invention are preferably aqueous, i.e. they have water or an aqueous solution or a lyotropic liquid crystalline phase as their major component. Suitably, the composition will comprise from 50 to 98 wt %, preferably from 60 to 90 wt % water based on the total weight of the composition.

Silicone

The anti-dandruff hair compositions may additional comprise from 0.1 to 10 wt %, preferably from 0.1 to about 8 wt %, more preferably from about 0.3 to about 5 wt % of a silicone.

Preferred suitable silicones may include polyalkyl siloxanes, polyaryl siloxanes, polyalkylaryl siloxanes, polyether siloxane copolymers, amino silicones and mixtures thereof.

The silicone may be present as the free silicone oil, or in the form of a silicone emulsion.

Preferably the silicone is present in the form of a silicone emulsion, more preferably an aqueous surfactant stabilized emulsion of silicone particles having a number average particle diameter ranging from 10 to 1,000 nm, most preferably from about 100 to about 500 nm.

Amino silicones are often formulated in hair compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions or microemulsions of dimethiconol. Also suitable are amodimethicone emulsions such as DC939 (from Dow Corning) and SME253 (from GE Silicones).

Suspending Agent

Preferably, the hair care composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent, if included, will generally be present in a hair care composition of the invention at levels of from 0.1 to 10 wt %, preferably from 0.5 to 6 wt %, more preferably from 0.9 to 4 wt % based on the total weight of the composition.

Non-Silicone Oily Conditioning Components

Compositions according to the present invention may also comprise a dispersed, non-volatile, water-insoluble oily conditioning agent.

This component will be dispersed in the composition in the form of droplets, which form a separate, discontinuous phase from the aqueous, continuous phase of the composition. In other words, the oily conditioning agent will be present in the shampoo composition in the form of an oil-in-water emulsion.

By "insoluble" is meant that the material is not soluble in water (distilled or equivalent) at a concentration of 0.1 percent (w/w), at 25° C. Suitably, the D3 2 average droplet size of the oily conditioning component is at least 0.4, preferably at least 0.8, and more preferably at least 1 micro m. Additionally, the D3 2 average droplet size of the oily conditioning component is preferably no greater than 10, more preferably no greater 8, more preferably no greater than 5, yet more preferably no greater than 4, and most preferably no greater than 3.5 μm.

The oily conditioning agent may suitably be selected from oily or fatty materials, and mixtures thereof.

Oily or fatty materials are preferred conditioning agents in the shampoo compositions of the invention for adding shine to the hair and also enhancing dry combing and dry hair feel.

Preferred oily and fatty materials will generally have a viscosity of less than 5 Pa·s, more preferably less than 1 Pa·s, and most preferably less than 0.5 Pa·s, e.g. 0.1 Pa·s and under as measured at 25 degrees centigrade with a Brookfield Viscometer (e.g. Brookfield RV) using spindle 3 operating at 100 rpm.

Oily and fatty materials with higher viscosities may be used. For example, materials with viscosities as high as 65 Pa·s may be used. The viscosity of such materials (i.e. materials with viscosities of 5 Pa·s and greater) can be measured by means of a glass capillary viscometer as set out further in Dow Corning Corporate Test Method CTM004, Jul. 20, 1970.

Suitable oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as C2 to C6 alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250 degrees centigrade to 300 degrees centigrade is termed mineral oil, and it consists of a mixture of hydrocarbons ranging from C16H34 to C21H 4. Suitable commercially available materials of this type include Sirius M85 and Sirius M125, all available from Silkolene.

Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages. Monocarboxylic acid esters include esters of alcohols and/or acids of the formula R'COOR in which R' and R independently denote alkyl or alkenyl radicals and the sum of carbon atoms in R and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate. Di- and trialkyl and alkenyl esters of carboxylic acids can also be used. These include, for example, esters of C4 to C8 dicarboxylic acids such as C7 to C22 esters (preferably C1 to C9) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol polyfatty add esters, ethoxylated glyceryl monostearate, 1,3-butylene glycol monostearate, 1,3-butylene glycol distearate, polyoxyethylene polyol fatty add ester, sorbitan fatty acid esters, polyoxyethylene sorbitan fatty acid esters and mono-, di- and triglycerides.

Particularly preferred fatty esters are mono-, di- and triglycerides, more specifically the mono-, di-, and tri-esters of glycerol and long chain carboxylic acids such as C7 to C22 carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soybean oil and coconut oil. The oily or fatty material is suitably present at a level of from 0.05 to 10, preferably from 0.2 to 5, more preferably from about 0.5 to 3 wt %.

The compositions of this invention preferably contain no more than 3 wt % of a styling polymer, more preferably less than 1 percent of a styling polymer, preferably contain less than 0.1 wt % styling polymer, and optimally are free of styling polymer.

In hair treatment compositions containing a conditioning agent, it is preferred that a cationic polymer also be present.

Adjuvants

The compositions of the present invention may also contain adjuvants suitable for hair care. Generally, such ingredients are included individually at a level of up to 2, preferably up to 1 wt % of the total composition.

Among suitable hair care adjuvants, are:
(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.
(ii) hair fibre benefit agents. Examples are: ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

Minor Ingredients

The compositions may also include other ingredients for enhancing performance and/or consumer acceptability. Such ingredients include fragrance (encapsulated or free or both), colorants, dyes and pigments, pearlescers or opacifiers, viscosity modifiers, stabilisers and preservatives. A suitable preservative system comprises Sodium Benzoate and Sodium Salicylate with pH adjustment using Sodium hydroxide and Citric Acid $H_2O$. An alternative preservation system comprising formaldehyde comprises: MIT and DMDM Hydantoin.

Product Forms

The hair care compositions may suitably be shampoos, conditioners, sprays, mousses, gels, waxes or lotions. Particularly preferred product forms are shampoos, post-wash conditioners (leave-in and rinse-off) and hair treatment products such as hair essences. Rinse off products are preferred and shampoos are particularly preferred.

Preferably, the compositions are free of, or substantially free of, hair styling polymer. The compositions are preferably formulated as compositions for the treatment of hair and subsequent rinsing.

A particularly preferred hair care composition is a shampoo composition. The total amount of surfactant in shampoo compositions of the invention (including any co-surfactant, and/or any emulsifier) is generally from 5 to 30 wt %, preferably from 10 to 25 wt %, more preferably from 15 to 20 wt % of the composition.

The invention will now be further described with reference to the following non-limiting examples.

EXAMPLES

Example

A. Preparation of Capsules

Capsules were prepared using the following materials. Material details and methods of preparation are outlined below.

|  | Example | |
| --- | --- | --- |
|  | Ex A | Ex 1 |
| Isocyanate | IDI | IDI |
| Isocyanate, g | 0.45 | 0.45 |
| Diamine | DETA | DETA |
| Diamine, g | 0.1 | 0.1 |
| Taurine, g | 0 | 0.02 |
| Method of preparation | I | II |

| Material reference | Chemical name |
| --- | --- |
| IDI | Isopherone diisocyanate |
| DETA | Diethyl triamine |
| Mowiol 8-88 | Poly(vinyl alcohol) |
| Propyl benzoate | Propyl benzoate |
| Piroctone | Piroctone |
| Tween-40 | Polyoxyethylenesorbitan monopalmitate |
| Methanol | Methanol |
| Taurine | Taurine |

Method of Preparation I

The following solutions were prepared:
Solution A: solution of 0.4 g Mowiol 8-88 in 39.6 g demineralized water.
Solution B: Piroctone (0.225 g), propyl benzoate (2.25 g) and isopherone diisocyanate (0.45 g).
Solution C: 10% DETA in demineralized water (1 mL).
Solution A was added to a 60 mL glass jar. Solution B was added to jar followed by homogenization with an IKA Ultra Turrax T25 basic on setting 1 at 11,000 rpm for 2 minutes (the jar itself was swirled gently during this time to aid homogenization). Solution C was added dropwise whilst stirring gently. The emulsion was stirred gently at room temperature for 1 h followed by 5 h at 35° C. before cooling.

Method of Preparation II

The following solutions were prepared:
Solution A: solution of 0.4 g Mowiol 8-88 in 39.6 g demineralized water.
Solution B: Piroctone (0.225 g), propyl benzoate (2.25 g) and isopherone diisocyanate (0.45 g)
Solution C: 10% DETA in demineralized water (1 mL).
Solution D: 2% taurine in demineralized water (1 mL).
Solution A was added to a 60 mL glass jar. Solution B was added to jar followed by homogenization with an IKA Ultra Turrax T25 basic on setting 1 at 11,000 rpm for 2 minutes (the jar itself was swirled gently during this time to aid homogenization). Solution C was added dropwise whilst stirring gently. Solution D was added dropwise whilst stirring gently. The emulsion was stirred gently at room temperature for 1 h followed by 5 h at 35° C. before cooling.

B. Method for the Determination of Capsule Collapse on Drying

A densely pack film of capsule is formed and imaged wet using a microscope on bright-field mode with cross-polarized filters, which gives a completely black image as no light is polarized by crystals. Upon drying the broken or collapsed capsules release piroctone which crystalizes, appearing white. A binary analysis of these images gave a % coverage of white and black, which can infer proportion of collapsed capsules in a dry sample.

The following programme was run on ImageJ software to perform this binary area analysis.
1. Open image
2. Image>Type>8-bit
3. Process>Binary>Options—check black background
4. Image>Adjust>Threshold—(make sure white and black areas correctly correspond to polarisation.
5. Edit>Selection>Create Selection
6. Analyse Measure (this gives white area in pixels)
7. White pixels/Total pixels=Collapse %.

|  | Example | |
|---|---|---|
|  | Ex A | Ex 1 |
| Collapse, % | 84.48 | 3.36 |

These results demonstrate that the presence of taurine can reduce the collapse of microcapsules when dry and hence the release of piroctone.

C. Method for the Determination of Piroctone Release from Capsule in Surfactant Solution The following solution was prepared:
Solution A; 5 mL of water added to 95 mL of methanol.
A Calibration Curve was Prepared:
0.0562 g of piroctone was dissolved in solution A in a 100 mL volumetric flask. Samples for the calibration curve were made by serial dilution on the 10 mL scale at concentrations of 56.2, 44.96, 33.72, 22.48, 11.24, 5.62, 2.81, 1.40 µg/mL. The absorbance of each solution was measured at λmax=303 nm.

| Piroctone concentration, mg/mL | Absorbance (303 nm) |
|---|---|
| 56.2 | 1.706708 |
| 44.96 | 1.3673724 |
| 33.72 | 1.0280368 |
| 22.48 | 0.6887012 |
| 11.24 | 0.3493656 |
| 5.62 | 0.1796978 |
| 2.81 | 0.0948639 |
| 1.4 | 0.052296 |

The calibration curve was determined to be Abs 300 nm=0.03019[piroctone]−0.01003

Measurement of Capsule Leakage 1 mL of microcapsule dispersion was taken immediately after synthesis and added to an 8 mL amber vial. To this, 5 mL of 1 w/w % TWEEN-40 solution was added and the vial was sealed for 48 h. After 48 h, the dispersion was filtered with a 0.45 µm PTFE syringe filter and 100 uL was added to 900 uL of solution A.

This solution was analyzed by UV-Vis spectrophotometry at 303 nm using a Cary 60 UV-Vis spectrophotometer. The absorbance result was converted to concentration (mg/mL via calibration curve not reported here) and % leakage derived by dividing by the concentration of total piroctone (5.62 mg/mL).

|  | Example | |
|---|---|---|
|  | Ex A | Ex 1 |
| Leakage, % | 1.2 | 1.28 |

Example 2

Example 2 is a shampoo composition according to the invention.

| Ingredient | wt % |
|---|---|
| SLES | 14.00 |
| Carbopol 980 | 0.60 |
| Tego betaine (CAPB) | 1.60 |
| Silicone DC1788 | 2.20 |
| Guar hydroxypropyl chloride | 0.20 |
| Perfume and minor ingredients | 2.35 |
| Encap Piroctone according to Example 1 | 0.3 |
| Water | To 100 |

The invention claimed is:

1. A core shell microcapsule having a liquid core and an outer shell, in which the liquid core comprises solvent and a dissolved piroctone compound; and
   the shell comprises polyurea comprising isocyanates, amines, and taurine, wherein the taurine is added during preparation of the shell at a level of 1 wt % to 5 wt % relative to isocyanate.

2. The core shell microcapsule according to claim 1 in which at most 8 times as much solvent by weight is used as piroctone compound is dissolved.

3. The core shell microcapsule according to claim 1 in which the isocyanate is an aliphatic isocyanate.

4. The core shell microcapsule according to claim 3 in which the aliphatic isocyanate is cyclic or branched.

5. The core shell microcapsule according to claim 1 wherein the solvent comprises an aromatic compound.

6. The core shell microcapsule according to claim 1 in which the weight ratio of solvent to piroctone compound within the shell microcapsule is at least 11:1.

7. The core shell microcapsule according to claim 1 wherein the shell has grafted to its outside surface a deposition aid.

8. The core shell microcapsule according to claim 1 in which the deposition aid is a cationic polymer.

9. The core shell microcapsule according to claim 1 wherein the shell is made by interfacial polymerisation.

10. A hair care composition comprising surfactant and at least 0.05 wt % of the total composition of a core shell microcapsule as described in claim 1.

11. The hair care composition according to claim 10 wherein the level of piroctone compound is from 0.01 wt % to 1.0 wt % of the total composition.

12. The hair care composition according to claim 10 wherein the hair care composition is an anti-dandruff shampoo.

13. The core shell microcapsule according to claim 2 in which at most 5 times as much solvent by weight is used as piroctone compound is dissolved.

14. The core shell microcapsule according to claim 1, wherein the solvent has a cLog P greater than 3.

15. The core shell microcapsule according to claim 1, wherein the solvent comprises heptanone.

16. The core shell microcapsule according to claim 1 in which the taurine is added during preparation of the shell at a level of 2 wt % relative to isocyanate.

\* \* \* \* \*